United States Patent [19]

Tamura et al.

[11] Patent Number: 5,648,230
[45] Date of Patent: Jul. 15, 1997

[54] ENDOTOXIN STABILIZING AGENT, ENDOTOXIN COMPOSITION AND METHOD FOR ASSAYING ENDOTOXIN

[75] Inventors: Hiroshi Tamura; Shigenori Tanaka; Jun Aketagawa; Toshio Oda, all of Tokyo, Japan

[73] Assignee: Seikagaku Kogyo Kabushiki Kaisha (Seikagaku Corporation), Tokyo, Japan

[21] Appl. No.: 474,722

[22] Filed: Jun. 7, 1995

[30] Foreign Application Priority Data

Jun. 30, 1994 [JP] Japan .................................. 6-150190

[51] Int. Cl.$^6$ ............................................. C12Q 1/34
[52] U.S. Cl. ................................................... 435/18
[58] Field of Search ........................................ 435/18

[56] References Cited

FOREIGN PATENT DOCUMENTS

| | | |
|---|---|---|
| 3350273 | 10/1990 | European Pat. Off. . |
| 513361 | 11/1992 | European Pat. Off. . |
| 552965 | 7/1993 | European Pat. Off. . |
| 569033 | 11/1993 | European Pat. Off. . |
| 958575 | 5/1964 | United Kingdom . |

OTHER PUBLICATIONS

"Laboratory of Reference Reagents", *DPQC/CBER/FDA Product Informatuon Circular*, May 23, 1995.

*Primary Examiner*—Johann Richter
*Assistant Examiner*—Ebenezer Sackey
*Attorney, Agent, or Firm*—Sughrue, Mion, Zinn, Macpeak & Seas

[57] ABSTRACT

An endotoxin stabilizing agent is provided, which is useful in order to maintain the endotoxin activity of a specimen or a reference standard in a stable state for a prolonged period of time and to prepare an endotoxin reference standard having a reduced interval variation, being stable for a long time in the form of, in particular, a solution and withstanding repeated use. An endotoxin composition comprising the above-mentioned endotoxin stabilizing agent and endotoxin and a method for assaying endotoxin by using the same are also provided. The endotoxin stabilizing agent comprises: (1) at least one substance selected from the group consisting of aminoalcohols, polyhydric alcohols, nonionic surfactants, polysucroses and chelating agents; (2) at least aminoalcohol and polyhydric alcohol; (3) with the polyhydric alcohol being preferably glycerol or its derivative; (4) polyethylene glycol as an effective ingredient in addition to the components (1) to (3); or (5) at least polysucrose, and an alkaline earth metal salt and/or polyethylene glycol as an effective ingredient. The endotoxin composition comprises the above-identified endotoxin stabilizing agent. The method for assaying endotoxin comprises adding the above-described endotoxin stabilizing agent to a specimen to thereby stabilize the activity of endotoxin in the specimen.

11 Claims, 1 Drawing Sheet

ENDOTOXIN STABILIZING AGENT, ENDOTOXIN COMPOSITION AND METHOD FOR ASSAYING ENDOTOXIN

FIELD OF THE INVENTION

This invention relates to the stabilization of endotoxin which is contained in a specimen or used as a reference standard. For example, it relates to an endotoxin stabilizing agent for stabilizing endotoxin in an endotoxin reference standard or a specimen, which is to be used in an assay of endotoxin by limulus reaction with the use of horseshoe crab amebocyte lysate, an endotoxin composition comprising endotoxin and a stabilizing agent, and a method for assaying endotoxin with the use of the same. In particular, it relates to an improved means for maintaining an endotoxin reference standard to be quantitatively assayed in a constant dispersion state, maintaining the endotoxin activity for the limulus reaction stable and, furthermore, in the endotoxin assay for safe management of specimens for clinical examinations requiring routine management, mainly a dialyzate resulted from hemodialysis (artificial dialysis), maintaining the endotoxin activity in a dialyzate stable and performing appropriate medical management.

BACKGROUND OF THE INVENTION

There has been known a method for assaying endotoxin, which is a pyrogen, by using horseshoe crab amebocyte lysate (hereinafter referred to simply as lysate). This method has been employed as an official method as a substitute for the rabbit pyrogem test. This assay method is based on a reaction (hereinafter referred to as limulus reaction) of the coagulation of the lysate due to a trace amount of endotoxin. Subsequent biochemical studies have revealed that this reaction consists of stepwise activation of several coagulation factors (FIG. 1) [Takanori Nakamura, Nippon Saikingaku Zasshi (Japanese Journal of Bacteriology), 38, 781–803 (1983)]. The endotoxin serving as the trigger in this reaction is an outer membrane component of the cell wall of a gram negative bacterium and also called lipopolysaccharide (LPS). It is an amphiphathic substance having both of a hydrophilic sugar chain and a hydrophobic lipid A moiety in its molecule. Under normal conditions, subunits of the LPS form an extremely large molecular association of $10^8$ dalton via hydrophobic bonding, ionic bonding, etc. It is known that these subunits form a complicated micelle together with the proteins and lipids coexisting therewith. This micelle structure largely affects the reactivity of the LPS in the limulus reaction (hereinafter referred to as limulus activity) and there exist a molecular size attaining the maximum activity and the micelle structure thereof. When an anionic surfactant, such as cholic acid or deoxychollc acid, is added, the association is completely dissociated into monomers or dimers and thus the limulus activity is completely lost. An unstable micelle not only causes changes in the assay data but also damages the stability of the endotoxin solution per se. In 1981, the Federal Food and Drug Administration (U.S.A.) attempted to improve an endotoxin reference standard originating in the E. coli 0113 strain by replacing the conventional additive albumin by lactose and polyethylene glycol to thereby stabilize the endotoxin activity. The reference standard thus obtained has been distributed by FDA as United States Pharmacopeia (USP) reference standard EC-5. In Japan, an attempt was made to employ mannitol as a filler of an endotoxin reference standard originating in E. coli UKT-B so as to stabilize the endotoxin activity by National Institute of Hygienic Science in 1988. The obtained product has been widely used as a reference standard of The Pharmacopoeia of Japan (JP).

However, USP and JP reference standards should be diluted prior to the assay, since they contain endotoxin at such a high concentration as 10,000 endotoxin unit (EU) per vial and 16,000 EU per vial, respectively. Thus dilution errors are unavoidable, which seriously hinders such an assay requiring a high accuracy and a high reproducibility as the quantitative limulus test. Namely, it is preferable to use an endotoxin reference standard which has been prepared in such a manner as to give a very low concentration. Thus, it has been required to develop a stable and highly reproducible additive therefor.

It is also known that when an endotoxin solution is dissolved in water and allowed to stand as such, the endotoxin activity of the aqueous solution is lowered within a short period of time, in particular, at a low concentration. Thus an endotoxin solution is generally prepared immediately before using and, after using, the residue should be discarded because of its poor stability, which not only requires a troublesome post-treatment but also causes economical disadvantage.

Accordingly, attempts have been made to store endotoxin in a lyophilized state to thereby solve the above-mentioned problems encountering in the case of the aqueous solution. However, there arises another problem, i.e., enlarged intervial variation. Namely, at a low endotoxin concentration, the content of endotoxin widely varies from vial to vial due to the scattering of the endotoxin powder.

There arises another problem that a lyophilized product cannot completely be dissolved upon use in some cases.

It is known in the field of medical services that routine control of endotoxin in body fluids is important in diagnosis of the symptoms of infectious diseases, in particular, sepsis, treatments of these diseases, judgement of the prognosis thereof, postoperative monitoring, etc. Also, it is essentially required in the safety management of dialyzates for patients under hemodialysis. In recent years, it is pointed out that the endotoxin activity in a dialyzate is unstable and lowered with the passage of time. It is therefore difficult to accurately determine endotoxin in a dialyzate, which seriously hinders the proper management of the dialyzate.

SUMMARY OF THE INVENTION

An object of the present invention is to provide an endotoxin stabilizing agent, which is useful for maintaining the endotoxin activity of a specimen or a reference standard in a stable state for a prolonged period of time and preparing an endotoxin reference standard having a relieved interval variation, being stable for a long time in the form of, in particular, a solution and withstanding repeated use, an endotoxin composition comprising the above-mentioned endotoxin stabilizing agent and endotoxin, and a method for assaying endotoxin by using the same.

The objects of the present invention can be achieved by the following agents:

1) an endotoxin stabilizing agent comprising at least one substance selected from the group consisting of aminoalcohole, polyhydric alcohols, nonionic surfactants, polysucroses and chelating agents as an effective ingredient;

2) the endotoxin stabilizing agent as described in the above 1) which comprises at least aminoalcohol and polyhydric alcohol;

3) the endotoxin stabilizing agent as described in the above 1) or 2) wherein said polyhydric alcohol is glycerol or a derivative thereof;

4) the endotoxin stabilizing agent as described in any of the above 1) to 3) further comprising polyethylene glycol as an effective ingredient;

5) the endotoxin stabilizing agent as described in the above 1) which comprises at least polysucrose, and an alkaline earth metal salt and/or polyethylene glycol;

6) an endotoxin composition comprising at least endotoxin and the endotoxin stabilizing agent comprising at least one substance selected from the group consisting of aminoalcohols, polyhydric alcohols, nonionic surfactants, polysucroses and chelating agents as an effective ingredient;

7) the endotoxin composition as described in the above 6) which is in the form of a dried matter or a liquid;

8) a method for assaying endotoxin which comprises adding to a specimen an endotoxin stabilizing agent comprising at least one substance selected from the group consisting of aminoalcohols, polyhydric alcohols, nonionic surfactants, polysucroses and chelating agents as an effective ingredient to thereby stabilize endotoxin in the specimen.

9) the method for assaying endotoxin as described in the above 8) wherein a limulus reagent is used.

10) the method for assaying endotoxin as described in the above 8) wherein said specimen is a dialyzate of hemodialysis.

11) a kit for assaying endotoxin which comprises at least a limulus reagent and an endotoxin stabilizing agent comprising at least one substance selected from the group consisting of aminoalcohols, polyhydric alcohols, nonionic surfactants, polysucroses and chelating agents as an effective ingredient.

DETAILED DESCRIPTION OF THE INVENTION

Figure 1:
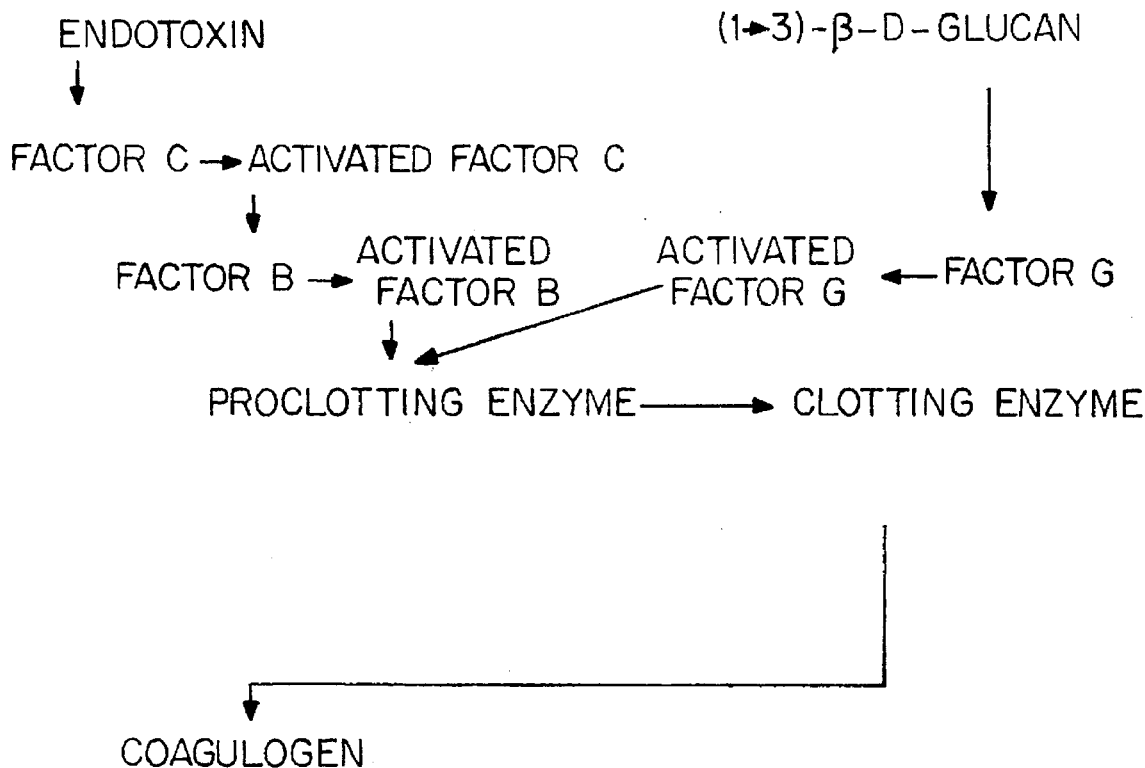
FIG. 1 shows the reaction mechanism of horseshoe crab amebocyte lysate with endotoxin and $(1-3)$-$\beta$-D-glucan.
Figure 1:
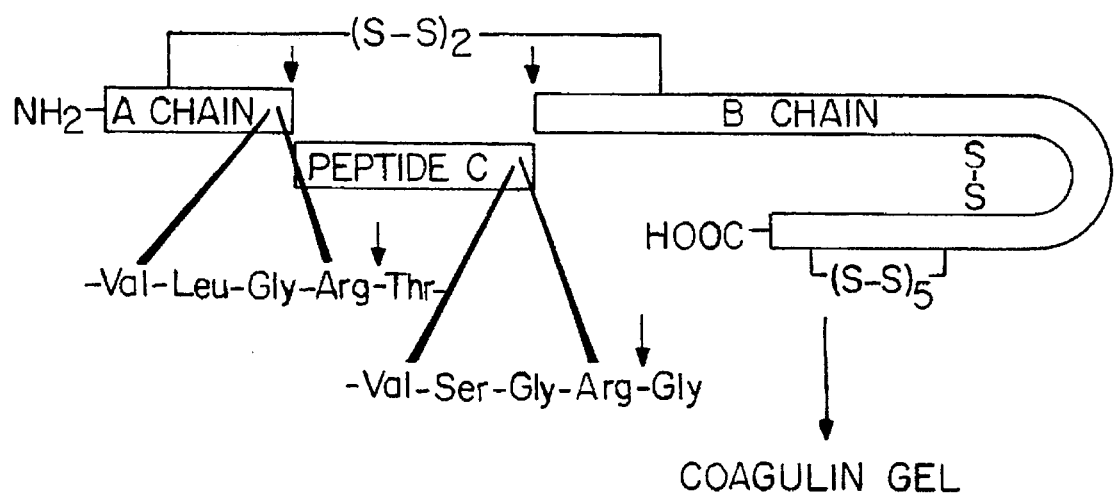

Specifically preferable examples of the endotoxin stabilizing agent of the present invention are as follows.

(1) An endotoxin stabilizing agent containing at least aminoalcohol, and polyhydric alcohols and/or polyethylene glycol as an effective ingredient [hereinafter referred to as the stabilizing agent (1)].

(2) An endotoxin stabilizing agent comprising glycerol or its derivative as an effective ingredient [hereinafter referred to as the stabilizing agent (2)].

(3) An endotoxin stabilizing agent comprising at least one chelating agent or nonionic surfactant as an effective ingredient [hereinafter referred to as the stabilizing agent (3)].

(4) An endotoxin stabilizing agent comprising at least one substance selected from the group consisting of aminoalcohols, chelating agents and nonionic surfactants as an effective ingredient, and polyethylene glycol [hereinafter referred to as the stabilizing agent (4)].

(5) An endotoxin stabilizing agent comprising polyethylene glycol and an alkaline earth metal salt as an effective ingredient [hereinafter referred to as the stabilizing agent (5)].

(6) An endotoxin stabilizing agent comprising polysucrose, polyethylene glycol and an alkaline earth metal salt as an effective ingredient [hereinafter referred to as the stabilizing agent (6)].

The endotoxin stabilizing agent according to the present invention [hereinafter the endotoxin stabilizing agent involving the above-mentioned stabilizing agents (1) to (6) will be sometimes referred to as the stabilizing agent in general] can be appropriately used in a reference standard for assaying endotoxin and for stabilizing endotoxin contained in general assay specimens.

The stabilizing agent may be used in an arbitrary manner. It may be used as either a solid as such or as a solution, preferably an aqueous solution. When it is to be used in a solid form, it may be taken up in a definite amount and added to a specimen. However, it is convenient that a definite amount of the stabilizing agent, which may be in the form of a solution, is previously taken up into a container. When the stabilizing agent is in the form of a solution, a pH of the solution is adjusted to range from 4 to 9, preferably from 6 to 8.

When the endotoxin composition of the present invention is to be used as a reference standard for quantitatively assaying endotoxin, the content of endotoxin in the composition should be preliminarily known. When the endotoxin composition is used for other purposes, for example, qualitative assay, it is not necessary that the endotoxin content is preliminarily known. The content of endotoxin in the reference standard is usually determined prior to the formulation of the endotoxin composition, though it may be determined after the formulation of the same. Although the endotoxin may be one originating in any source without restriction, use can be generally made of those prepared from gram negative bacteria such as *Escherichia coli* and microorganisms belonging to the genus Salmonella by a publicly known method.

The endotoxin composition of the present invention can be obtained in the form of a solution or lyophilizate by mixing the stabilizing agent with an aqueous suspension of the above-mentioned endotoxin preparation or a lyophilized product of the same. In the preparation, the components of the endotoxin composition may be added in an arbitrary order.

When suspended in water, the endotoxin composition prepared in accordance with the present invention shows uniform dispersibility and exhibits a stable limulus activity for a prolonged period of time. Similarly, a lyophilized powder thereof sustains stable properties for a long time even at a relatively high temperature, i.e., room temperature or above.

When suspended in water, for example, the endotoxin composition remains stable at least for 2 weeks at 4° C. When lyophilized, it remains stable at least for 2 weeks at 40° C. and at least for 3 years at 4° C.

Further, the stabilizing agent of the present invention is usable in the stabilization of endotoxin contained in a specimen. More specifically, when a specimen for a clinical examination, for example, a dialyzate in hemodialysis, is collected, the stabilizing agent, which may be in the form of either a solid or a solution, is preliminarily distributed in a container, which may be made of an appropriate material such as glass, polypropylene, polystyrene or polyethylene without limitation, to thereby stabilize endotoxin in the specimen. The endotoxin solution thus stored is not affected by metal ions, for example, iron ion, which may possibly be incorporated at the sampling of the specimen, or trace elements originating in the container. Thus it can sustain uniform dispersibility and activity. The method for assaying endotoxin of the present invention in which a specimen is stabilized by the stabilizing agent of the present invention can be effected with stably maintaining, for example, the specimen for at least 15 days at 4° C. Endotoxin can be assayed by using the limulus reaction.

The effective ingredients of the endotoxin stabilizing agent of the present invention will be described in detail.

The aminoalcohol is not particularly restricted, so long as it is a compound having an amino group and a hydroxyl group. Preferable examples thereof include triethanolamine, diethanolamine and 2-aminoethanol (monoethanolamine).

As polyhydric alcohol, tri-hydric alcohols and higher ones can be used. Preferable examples of polyhydric alcohols of low molecular weight include tri-to penta-hydric alcohols having a molecular weight of 50 to 500. Polyhydric alcohols of high molecular weight are exemplified by high molecular weight compounds having a hydroxyl group such as polyvinyl alcohol. Specific examples thereof include polyhydric alcohol of low molecular weight such as sugar alcohols (for example, mannitol, xylitol) and glycerol and its derivatives (for example, glycerol α-monochlorohydrin) and polyhydric alcohols of high molecular weight such as polyvinyl alcohol having an average molecular weight of 500 to 3500.

Examples of the nonionic surfactant include polyoxyethylene ethers (Brij-series surfactants, etc.; usually having a degree of polymerization of 8 to 40, those having an isooctylphenyl ether group as the terminal group being particularly preferable), polyoxyethylene sorbitan alkyl esters [Tween-series surfactants, etc.; monolaurate (Tween 20, 21), monopalmitate (Tween 40), monostearate (Tween 60, 80), etc.], polyoxyethylene p-t-octylphenyl ethers (Triton-series surfactants, etc.; Triton X-100, etc. being preferable) and alkylglucosides (n-octylglucopyranoside, n-dodecylglucopyranoside, etc.).

Polysucrose is a substance specified as Chemical Abstract Service (CAS) registry number 9012-95-7. It is also called Ficoll™ manufactured by Pharmacia) or sucrose polymer. In usual, it is synthesized by copolymerizing sucrose with epichlorohydrin. Although a number of polysucrose products differing in molecular weight from each other are commercially available, the molecular weight of the polysucrose to be used in the present invention is not particularly restricted. Specific examples thereof include Ficoll 400 (molecular weight: 400,000) and Ficoll 70 (molecular weight: 70,000).

The chelating agent is not particularly restricted, so long as it can undergo coordination to a metal ion to thereby form a stable complex. Examples thereof include EDTA (ethylenediaminetetraacetic acid), GEDTA [bis(2-aminoethyl)ethyleneglycoltetraacetic acid; glycol ether diaminotetraacetic acid], BAPTA (aminophenylethyleneglycoltetraacetic acid), citric acid, sodium citrate and NTA (nitrilotriacetic acid). Since metals (for example, iron) are frequently used in pipes of a hemodialyzer, a dialyzate is sometimes contaminated with a trace amount of metal ions. In such a case, the limulus activity of endotoxin in the specimen is lowered. The addition of the above-described chelating agent can prevent the decrease in the endotoxin activity caused by metal ions.

Examples of the alkaline earth metal salt include calcium chloride, strontium chloride and magnesium chloride.

The polyethylene glycol, which can achieve particularly preferable effects as the stabilizing agent of the present invention when used together with the above-mentioned components, is exemplified by polymers of ethylene glycol, such as dihydric alcohol, having an average molecular weight of from 200 to 2,000,000, preferably from 2,000 to 40,000 and more preferably from 4,000 to 20,000.

Each component to be used in the stabilizing agents (1) to (6) of the present invention and the ratio thereof to endotoxin may be optionally selected so as to give the most suitable stabilizing agent, but each component may be selected from among the above range almost in common to the stabilizing agent.

The stabilizing agent (1) of the present invention contains at least aminoalcohol, and polyhydric alcohols and/or polyethylene glycol as an effective ingredient. The stabilizing agent (1) of the present invention may have one of the following four compositions.

(1)-1: aminoalcohol.

(1)-2: aminoalcohol and polyhydric alcohol.

(1)-3: aminoalcohol and polyethylene glycol.

(1)-4: aminoalcohol, polyhydric alcohol and polyethylene glycol.

In the endotoxin composition containing the stabilizing agent (1) of the present invention or in a specimen to which the stabilizing agent, the concentration of the polyhydric alcohol ranges from 0.01 to 1 w/v% (hereinafter abbreviated as %), preferably from 0.05 to 0.2%, the concentration of the aminoalcohol ranges from 0.0001 to 0.1%, preferably from 0.0005 to 0.05% and the concentration of the polyethylene glycol ranges from 0,001 to 0.02%, preferably from 0.002 to 0.006%.

The stabilizing agent (2) of the present invention contains glycerol or its derivative as an effective ingredient. The concentration of the stabilizing agent (2) to be added to an endotoxin composition or a specimen falls within the same range as that of the stabilizing agent (1).

The stabilizing agent (3) of the present invention contains at least one substance selected from among chelating agents and nonionic surfactants as an effective ingredient.

In the endotoxin composition containing the stabilizing agent (3) of the present invention or in a specimen to which the stabilizing agent has been added, the concentration of the chelating agent ranges from 0.01 to 0.5 mM, preferably from 0.02 to 0.2 mM and the concentration of the nonionic surfactant ranges from 0.0005 to 0.2%, preferably from 0.001 to 0.04%.

The stabilizing agent (4) of the present invention contains at least one substance selected from the group consisting of aminoalcohols, chelating agents and nonionic surfactants as an effective ingredient, and polyethylene glycol. The stabilizing agent (4) of the present invention may have one of the following four compositions.

(4)-1: polyethylene glycol and chelating agent.

(4)-2: polyethylene glycol and nonionic surfactant.

(4)-3: polyethylene glycol, chelating agent and nonionic surfactant.

(4)-4: polyethylene glycol, chelating agent and aminoalcohol.

The concentration of each of the components of the stabilizing agent (4) to be added to an endotoxin composition or a specimen is the same as that of the stabilizing agent (1) or (3) as described above.

The stabilizing agent (5) of the present invention contains polyethylene glycol and an alkaline earth metal salt as an effective ingredient.

In the endotoxin composition containing the stabilizing agent (5) of the present invention or in a specimen to which the stabilizing agent has been added, the concentration of the polyethylene glycol ranges from 0.001 to 0.05%, preferably from 0.002 to 0.01% and the concentration of the alkaline earth metal salt ranges from 0.001 to 5 mM, preferably from 0.005 to 0.5 mM.

The stabilizing agent (6) of the present invention contains polysucrose, polyethylene glycol and an alkaline earth metal salt as an effective ingredient.

In the endotoxin composition containing the stabilizing agent (6) of the present invention or in a specimen to which the stabilizing agent has been added, the concentration of the polysucrose ranges from 0.005 to 0.5%, preferably from 0.01 to 0.1%, the concentration of the polyethylene glycol ranges from 0.001 to 0.05%, preferably from 0.002 to 0.01% and the concentration of the alkaline earth metal salt ranges from 0.001 to 5 mM, preferably from 0.005 to 0.5 mM.

The endotoxin composition to be used in the present invention may be prepared by adding the above-mentioned components of the stabilizing agent, either separately or in the form of a mixture which has been preliminarily formed, to an endotoxin solution, as described above. Alternatively, it may be obtained by preliminarily preparing a stabilizing agent mixture and then adding endotoxin thereto. The addition may be effected in an arbitrary order. Also, the order of the addition of the components of the stabilizing agent is not particularly restricted. It is appropriate to prepare the composition at a temperature of 0° to 50° C., preferably at 0° to 40° C. and more preferably at 10° to 25° C. After mixing these components together, the resulting mixture is usually stirred with, for example, a magnetic stirrer for 10 seconds to 15 minutes to thereby give a uniform mixture. It is also possible to suppress a decrease in the limulus activity of endotoxin and obtain a uniform dispersion by suppressing the abnormal heat generation. The pH of the endotoxin composition is adjusted to range from 4 to 9, preferably 6 to 8.

The endotoxin composition of the present invention may be dried by any method without restriction, so long as the activity of endotoxin is not lowered thereby. The endotoxin composition can be preferably dried by a method of dehydrating at a low temperature, with vacuum lyophilization being particularly preferred. Any vacuum lyophilizer (bench type, floor type, etc.) may be used therefor, so long as it achieves a definite degree of vacuum. As discussed above, the concentration of the stabilizing agent of the present invention is regulated to an extremely low level so as not to affect the limulus activity of endotoxin. However each component of the stabilizing agent as described above enhance the adhesiveness of endotoxin to a container, for example, a glass vial, and thus completely prevent the leakage of the composition from the container due to physical vibration, which solves the problem of the scattering of the powder upon lyophilization encountering in the conventional methods.

Accordingly, the present invention makes it possible to easily obtain a stable endotoxin composition suffering from little intervial variation in the data of the limulus activity of endotoxin. Thus the accuracy of the limulus test ten be highly elevated.

In order to maintain endotoxin in a specimen, for example, a dialyzate, stable by using the stabilizing agent of the present invention, a small amount of an aqueous solution of the stabilizing agent is preliminarily distributed into a container followed by lyophilization. Alternatively, the container containing the aqueous solution of the stabilizing agent is sealed as such. Neither the material of the container nor the order of addition is not particularly restricted.

In the present invention, the endotoxin composition thus prepared or the aqueous solution containing the stabilizing agent together with endotoxin is colorless, transparent and odorless. It not only has a uniform dispersibility and a high limulus activity but also remains stable in the form of a solution for a prolonged period of time. Moreover, the endotoxin composition of the present invention suffers from little assay variation, though it is contained in an extremely small amount in each vial. Thus it is usable as an endotoxin reference standard of a high accuracy. This composition can be simply and easily prepared in a large quantity.

The endotoxin assay can be carried out with high accuracy by using the kit comprising the above-described endotoxin stabilizing agent. The kit for assaying endotoxin according to the present invention comprises at least a limulus reagent and an endotoxin stabilizing agent comprising at least one substance selected from the group consisting of aminoalcohols, polyhydric alcohols, nonionic surfactants, polysucroses and chelating agents as an effective ingredient.

As described above, the present invention makes it possible to easily provide an endotoxin composition containing a small amount of the endotoxin reference standard which is capable of exerting a stable activity over a long period of time in the form of a solution by dispersing a small amount of endotoxin in a solvent containing a specific stabilizing agent to thereby maintain a stable micelle structure. According to the present invention, the variation of the endotoxin assay can be narrowed and few instruments are required for dilution. Also, the assay time can be shortened and a solution once formed can be reused. Thus the assay accuracy of the Limulus test can be highly elevated and, moreover, a number of advantages can be achieved from the viewpoints of assay time and assay cost.

The present invention provides a epoch-making solution to the problem of the stability of endotoxin in specimens which has been a serious obstacle encountering in the field of hemodialysis for the accurate assay of endotoxin in dialyzates. When a usual dialyzate is mixed with a solvent containing the specific stabilizing agent as described above, a stable micelle structure of the endotoxin contained in the dialyzate can be maintained and the adsorption of endotoxin by the container can be completely prevented. Thus the activity of endotoxin can be sustained for a prolonged period of time. Thus endotoxin in the dialyzate can be accurately assayed, which makes it possible to properly manage the safety of the dialysis system. In recent years, frequent use of high-flux membranes (high-performance membranes) made of hollow fibers having an enlarged pore size so as to elevate the ratio of eliminating harmful matters causes a problem of the back filtration of endotoxin toward a living body. The present invention provides a method and a tool for effective storage of endotoxin, which can obviate such a serious problem as described above and ensure the safety for human body.

To further illustrate the present invention, and not by way of limitation, the following Examples will be given.

EXAMPLE 1

Preparation of low content endotoxin composition and stability test thereof

To endotoxin prepared from *E. coli* UKT-B strain (JP reference standard endotoxin, 16,000 EU/vial, distributed by National Institute of Hygienic Science) was added 1.6 ml of distilled water for injection and the endotoxin was dissolved by thoroughly stirring (10,000 EU/ml). The solution thus obtained, which served as the stock solution, was appropriately diluted with distilled water and formulated into endotoxin solutions (3 EU/ml) containing 0.001% of triethanolamine (manufactured by Tokyo Kasei Koryo Co., Ltd.), 0.004% of polyethylene glycol 6,000 (manufactured by Wako Pure Chemical Industries, Ltd.), 0.1% of glycerol (manufactured by Wako Pure Chemical Industries, Ltd.) or various additives as listed in Table 1. Each mixture thus obtained was distributed into glass vials in 0.5 ml portions and lyophilized by using a vacuum lyophilizer (manufactured by Laboconco Corporation), To examine the interval variation of the composition of low endotoxin content, the endotoxin composition (6 vials) prepared by each method was dissolved in 3.0 ml of distilled water. A 10 μl portion of the solution was taken up from each vial and distributed into an endotoxin-free 96-well microplate (Toxipet plate 96F; commercially available by Seikagaku Corporation). Then, 100 μl of an endotoxin-specific chromogenic limulus reagent [the limulus reagent for the highly sensitive chromogenic synthetic substrate method using factors reacting exclusively with endotoxin in FIG. 1: Endospecy ES-200 (manufactured by Seikagaku Corporation) dissolved in 5.6 ml of a 0.1M Tris-hydrochloride buffer solution (pH 8.0)] was added thereto.

The resulting mixture was reacted at 37° C. for 30 minutes in an incubator installed in a microplate reader with a built-in analysis program (Well Reader SK601, commercially available by Seikagaku Corporation), the increase in absorbance by released chromogen at 405 nm (reference wavelength: 492 nm) was recorded to obtain the rate of the increase per min. and endotoxin concentration was automatically calculated from the calibration curve using a USP reference standard endotoxin (kinetic assay). After repeating this procedure 6 times, analytical data of 36 samples were obtained in all. The mean and the standard deviation of these data were calculated. Then the coefficient of variation (CV) was determined as an index of the interval variation. Separately, each endotoxin composition (4 vials) were dissolved in 3 ml of distilled water and stored at 4° C. for 7 days and 14 days. After the storage, the endotoxin activity of the solution was assayed as the limulus activity with the use of Endospecy. Then it was expressed in the relative value (residual limulus activity; %) to the limulus activity assayed by the same method before the storage. The storage stability of the endotoxin composition in the form of a solution was thus evaluated. Further, the above-mentioned endotoxin composition was stored at 40° C. for 14 days and at 70° C. for 3 days. Then the residual limulus activity (%) of each case was determined by the same method as described above. Thus the stability of the endotoxin composition in a dry state was evaluated.

TABLE 1

Storage stability of endotoxin composition

| Additive | Storage stability (residual activity, %) | | | | Interval variation | Remarks |
| | 4° C., soln | | 40° C. | 70° C. | | |
| | Day 7 | Day 14 | Day 14 | Day 3 | (CV. %. n = 6) | |
| --- | --- | --- | --- | --- | --- | --- |
| none | 58 | 38 | 24 | 17 | 15.1 | Comparison |
| 0.004% polyethylene glycol (Mw. 6,000) | 65 | 57 | 61 | 52 | 12.5 | |
| 0.001% triethanolamine | 90 | 89 | 76 | 65 | 13.8 | Invention |
| 0.1% glycerol | 92 | 91 | 87 | 85 | 6.9 | |
| 0.1% glycerol 0.001% triethanolamine | 98 | 98 | 98 | 96 | 5.0 | |
| 0.1% glycerol 0.001% triethanolamine 0.004% polyethylene glycol (Mw. 6,000) | 102 | 100 | 100 | 98 | 4.8 | |
| 0.01% mannitol 0.002% triethanolamine 0.005% polyethylene glycol (Mw. 20,000) | 98 | 98 | 98 | 97 | 5.4 | |
| 5 mM sodium citrate | 95 | 95 | 93 | 89 | 9.6 | |
| 5 mM sodium citrate 0.005% polyethylene glycol (Mw. 6,000) | 98 | 98 | 96 | 95 | 5.7 | |
| 0.003% Triton X-100 0.005% polyethylene glycol (Mw. 6,000) | 99 | 99 | 96 | 95 | 5.9 | |

As Table 1 shows, the endotoxin compositions containing the stabilizing agents (1) to (4) of the present invention have been improved in the storage stability of endotoxin and the interval variation, compared with the product containing polyethylene glycol alone as a stabilizing agent or the product containing no stabilizing agent. It can be seen that the present invention makes it possible to easily prepare an endotoxin composition with a low content which remains stable for a prolonged period of time even in the form of a solution and has an excellent storage stability at a high temperature in the form of a lyophilized product. It can be also found that the present invention makes it possible to obtain a dry endotoxin composition with a high reproducibility and an extremely small interval variation, even though a very small amount of endotoxin is distributed and lyophilized.

EXAMPLE 2

Effects of various additives on the stability of endotoxin in dialyzate

In a usual hemodialysis, dialyzates were collected in glass test tubes in which various additives were contained, from a coupler in the dialyzate-supply side of a console. Then, these dialyzates were stored at 4° C. for 1 day, 5 days and 15 days. The endotoxin activity was assayed in the same manner as the one described in Example 1 by using Endospecy. Thus the residual activity was calculaned by referring the dialyzate containing no additive as a control.

TABLE 2

Effects of various additives on the stability of dialyzate

| | Residual activity (%) at 4° C. | | | |
|---|---|---|---|---|
| Additive | after 1 day | after 5 days | after 15 days | Remarks |
| none | 58 | 47 | 12 | Comparison |
| 0.007% Ficoll | 65 | 56 | 26 | |
| 0.003% triethylamine | 61 | 50 | 18 | |
| 0.2 mM calcium chloride | 58 | 45 | 16 | |
| 0.5 mM magnesium sulfate | 59 | 45 | 12 | |
| 0.01 mM strontium sulfate | 60 | 49 | 16 | |
| 0.04% dextran | 60 | 52 | 14 | |
| 0.001% triethanolamine | 95 | 95 | 86 | Invention |
| 0.002% Triton X-100 | 95 | 92 | 85 | |
| 0.02% Tween 20 | 98 | 92 | 67 | |
| 0.005 2 N-octyl-β-D-glucoside | 95 | 91 | 86 | |
| 0.05 mM EDTA | 95 | 93 | 56 | |
| 0.05 mM sodium citrate | 96 | 95 | 58 | |
| 0.007 mM calcium chloride 0.007% polyethylene glycol (Mw. 6,000) | 98 | 97 | 94 | |
| 0.005% triethanolamine 0.007% polyethylene glycol (Mw. 20,000) | 98 | 98 | 95 | |
| 0.05 mM NTA 0.007% polyethylene glycol (Mw. 6,000) | 97 | 96 | 94 | |

TABLE 3

Effects of various additives on the stability of dialyzate

| | Residual activity (%) at 4° C. | | | |
|---|---|---|---|---|
| Additive | after 1 day | after 5 days | after 15 days | Remarks |
| A: 0.1% glycerol 0.001% triethanolamine 0.004% polyethylene glycol (Mw. 6,000) | 100 | 100 | 99 | Invention |

TABLE 3-continued

Effects of various additives on the stability of dialyzate

| | Residual activity (%) at 4° C. | | | |
|---|---|---|---|---|
| Additive | after 1 day | after 5 days | after 15 days | Remarks |
| B: 0.07% Ficoll 0.007 mM strontium chloride 0.007% polyethylene glycol (Mw. 6.000) | 100 | 100 | 98 | |
| C: 0.002% triethanolamine 0.1 mM EDTA 0.005% polyethylene glycol (Mw. 4,000) | 100 | 100 | 98 | |
| D: 0.001% triethanolamine 0.1 mM sodium citrate 0.005% polyethylene glycol (Mw. 4,000) | 100 | 100 | 98 | |
| E: 0.15 mM GEDTA 0.01% Tween 85 0.004% polyethylene glycol (Mw. 6,000) | 100 | 100 | 97 | |

As Tables 2 and 3 show, each case that the stabilizing agent of the present invention had been distributed into the containers indicated little change in the limulus activity after storing at 4° C. for 5 days. Thus a considerably improved protecting effect was observed in such a case, compared with the one free from any stabilizing agent. It has been also clarified that the mixture A containing the stabilizing agent (1), the mixture B containing the stabilizing agent (6) and the mixtures C, D and E containing the stabilizing agent (4) each can sustain an activity at a definite level over a long period of time (15 days).

While the invention has been described in detail and with reference to specific examples thereof, it will be apparent to one skilled in the art that various changes and modifications can be made therein without departing from the spirit and scope thereof.

What is claimed is:

1. An endotoxin stabilizing agent comprising at least one substance selected from the group consisting of aminoalcohols, polyhydric alcohols, nonionic surfactants, polysucroses and chelating agents as an effective ingredient.

2. An endotoxin stabilizing agent as claimed in claim 1 which comprises at least aminoalcohol end polyhydric alcohol.

3. An endotoxin stabilizing agent as claimed in claim 1 or 2 wherein said polyhydric alcohol is glycerol or a derivative thereof.

4. An endotoxin stabilizing agent as claimed in claim 1, 2 or 3 which further comprises polyethylene glycol as an effective ingredient.

5. An endotoxin stabilizing agent as claimed in claim 1 which comprises at least polysucrose, and an alkaline earth metal salt and/or polyethylene glycol.

6. An endotoxin composition comprising at least endotoxin and an endotoxin stabilizing agent comprising at least one substance selected from the group consisting of aminoalcohols, polyhydric alcohols, nonionic surfactants, polysucroses and chelating agents as an effective ingredient.

7. An endotoxin composition as claimed in claim 6 which is in the form of a dried matter or a liquid.

8. A method for assaying endotoxin which comprises adding to a specimen an endotoxin stabilizing agent comprising at least one substance selected from the group consisting of aminoalcohols, polyhydric alcohols, nonionic surfactants, polysucroses and chelating agents as an effective ingredient to thereby stabilize endotoxin in the specimen.

9. A method for assaying endotoxin as claimed in claim 8 wherein a limulus reagent is used.

10. A method for assaying endotoxin as claimed in claim 8 wherein said specimen is a dialyzate of hemodialysis.

11. A kit for assaying endotoxin which comprises at least a limulus reagent and an endotoxin stabilizing agent comprising at least one substance selected from the group consisting of aminoalcohols, polyhydric alcohols, nonionic surfactants, polysucroses and chelating agents as an effective ingredient.

* * * * *